United States Patent [19]

Gozzini et al.

[11] Patent Number: 5,780,644

[45] Date of Patent: Jul. 14, 1998

[54] BRANCED POLYOXAALKYL MACROMOLECULES

[75] Inventors: Luigia Gozzini; Monica Muttoni; Christoph DeHaën, all of Milan, Italy

[73] Assignee: Dibra S.p.A., Italy

[21] Appl. No.: 404,259

[22] Filed: Mar. 15, 1995

[30] Foreign Application Priority Data

Mar. 18, 1994 [IT] Italy .................. MI94 A 0512

[51] Int. Cl.[6] .................. C07D 209/48; C07D 315/00; C07C 303/00; C07C 43/11

[52] U.S. Cl. .................. 548/478; 548/473; 549/415; 558/46; 564/505; 568/32; 568/614; 568/623; 568/624

[58] Field of Search .................. 568/623, 28; 558/46; 548/473; 549/416; 564/505

[56] References Cited

U.S. PATENT DOCUMENTS

| 4,737,550 | 4/1988 | Tomalia | 525/418 |
|---|---|---|---|
| 5,099,042 | 3/1992 | Wardle et al. | 552/11 |
| 5,294,365 | 3/1994 | Welch et al. | 252/174.21 |

*Primary Examiner*—Johann Richter
*Assistant Examiner*—Joseph Murray
*Attorney, Agent, or Firm*—Nixon & Vanderhye

[57] ABSTRACT

Branched, dendrimeric-type macromolecules composed essentially of a central nucleus and of a series of polyoxaalkyl chains that depart from said nucleus and spread into the surrounding space branching in a cascade fashion useful as carriers of drugs, contrast agents, etc.

8 Claims, No Drawings

BRANCED POLYOXAALKYL MACROMOLECULES

The present invention concerns a new class of branched, dendrimeric-type macromolecules composed essentially of a central nucleus and of a series of polyoxaalkyl chains that depart from said nucleus and spread into the surrounding space branching in a cascade fashion until the desired size is obtained. The molecules formed in this way do not have excessive functional crowding on their outer surfaces. The invention also includes the synthetic method for obtaining these molecules as well as their uses.

Over the past decade dendrimeric macromolecules have stirred considerable interest because of their intrinsic features which are very different from those of highly polydispersed linear or branched polymers produced by polymerisation processes. On the contrary, dendrimers are obtained through synthetic procedures involving a step-by-step growth which allow for greater control over molecular mass, size and shape. Dendrimeric molecules are characterized by having a central nucleus, termed "core", from which chains originate and branch off to the periphery to occupy all the available space. This leads to a multibranched ordered structure having many functional groups on the external surface. Such a molecule can have a highly congested surface capable of controlling the diffusion of small chemical entities into and out of the dendrimeric structure. Depending on the kind and dimension of their constituents, such macromolecules can assume different geometric shapes (spheroidal, cylindrical, mushroom-like, ellipsoidal etc.). Compared with other branched polymers, these macromolecules usually are endowed with a relatively low intrinsic viscosity (limiting viscosity number) even at high molecular masses.

Macromolecules with different denominations, synthesized and patented by different research groups can be included in this class of derivatives. The main classes are shown in Table I.

TABLE I

Main classes of dendrimeric macromolecules

| Denomination | Research group | References | Main patents | Chemical structures |
|---|---|---|---|---|
| Starburst | Tomalia | 1–5 | US 4,587,329 | Starburst dendrimers include: polyamidoamines (PAMAM), polyethyleneimines (PEI), polyethers (PE) polythioethers. |
| Denkewalter dendrimers | Denkewalter | 6 | US 4,289,872 | Lysine-based branched polymers. |
| Arborols | Newkome | 7–12  29 | WO 9321144 | Arborols include molecules having either a benzene "core" or a "core" with four saturated hydrocarbon branches. |
| Dendrimeric poliethers | Fréchet | 13–19 | US 5,041,516  WO 9208749  WO 9321259 | Functionalized benzenes poliethers synthesized through an original synthetic approach (convergent synthesis). |
| DSM dendrimers | De Brabander-van den Berg | 30 | WO 9314147 | Poly(propylene imine) dendrimers with branches prepared from vinyl cyanide units. |

Starburst Dendrimers (Ref. 1–5)

Starburst dendrimers synthesized by Tomalia et al. include:

a) Starburst polyamidoamine (PAMAM) dendrimers (Ref. 1-3)

These are compounds with either a nucleophilic or an electrophilic "core". One of the most widely used nucleophilic "core" is ammonia. In this case, the synthesis involves a preliminary reaction with methyl acrylate (Michael's addition) to form a triester which is then amidated with ethylenediamine to form a first generation molecule containing 3 terminal amino groups (Scheme 1).

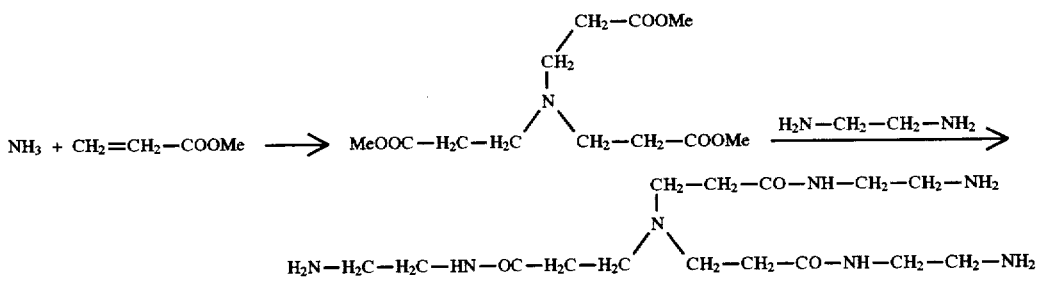

Scheme 1

By repeating these synthetic steps the dendrimer grows in diameter by approximately 10 Å per generation evolving from an undefined shape for generations 0–2 to an oblate spheroid for generations 3–4 and finally to a nearly symmetrical spheroid for generations 5 and higher. Another example of "core" is ethylenediamine.

b. Starburst polyethyleneimine PEI) dendrimers (Ref. 1)

These molecules derive from a symmetrical "core" comprising 3 amino functions, obtained through alkylation of diethylenetriamine with aziridine. The first generation is obtained by reacting this "core" with N-tosylaziridine or N-mesylaziridine and by subsequent deprotection (Scheme 2).

Scheme 2

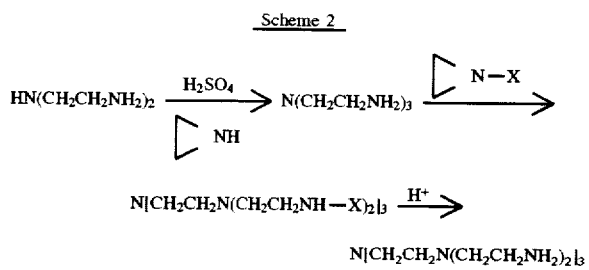

x=tosyl or mesyl

The higher generations are obtained by repeating these synthetic steps. PEIs differ from PAMAMs because of their short branch-segment lengths. For each generation, the diameter increases by only 5 Å compared with the 10 Å of PAMAMs. The CPK® (Corey Pauling Koltun) models indicate that these dendrimers are much more compact and congested than the starburst PAMAMs. These models show that the 5th generation is impossible due to the so-called "dense-packing" phenomenon or excessive crowding of surface functional groups, phenomenon which makes impossible or only partially possible the further growth of the molecule (Ref. 1). Compared with PAMAMs, PEIs possess more stable chemical bonds.

c) Starburst polyether dendrimers (Ref. 1, 4, 5)

These dendrimers are examples of macromolecules endowed with the maximum packing effect due to the high multiplicity of the "core" (4 functional groups), and of the branching points (3 functional groups per unit). This gives rise to very compact molecules having highly congested microdomains which possess only very small internal voids. The starting compound, pentaerythritol tetrabromide, is reacted with pentaerythritol molecules in which the 3 hydroxyl functions are protected as orthoesters. The resulting molecule assumes a spheroidal shape from the first generation. As a consequence by the fourth generation, which should possess 324 hydroxy groups on the external surface, a highly constrained and rigid system with no internal voids or channels should be formed. Indeed, the fourth generation cannot itself be obtained because of excessive steric hindrance on the external surface. Synthetic studies revealed that branching defects became progressively higher as one advanced from generation 2 to generation 3.

d) Starburst polythioether dendrimers (Ref. 1)

These are similar to the polyethers except that a mercaptobicyclic orthoester is used for the coupling step instead of the hydroxybicyclic orthoester. In this way, a dendrimer containing thioether bonds and hydroxyl groups on the external surface is obtained. In the case of polythloether dendrimers, the molecules are already hindered by the second generation and attempts to obtain the third generation have so far been unsuccessful. The main difference between PAMAMs and polyether and polythioether dendrimers is that the latter molecules assume a congested structure starting already from the first generation and have almost no internal voids. They are therefore much more compact molecules.

Denkewalter's dendrimers (Ref. 6)

Denkewalter et al. (Ref. 6) reported the synthesis of lysine-based dendrimers obtained by using the classic approach for solid-phase peptide synthesis. The lysine trees were constructed using a benzhydrylamine resin and N-protected tert-butyloxycarbonyl lysine. The branching points, i.e. the lysine amino groups, are located on segments of different length.

Polyamidoalcohol dendrimers (arborols) (Ref. 7-12, 29)

They have been synthesized by Newkome and co-workers. This class of dendrimers is an example of a heterogeneous series of highly branched compounds with a large number of functional groups on the external surface. In the literature, only low-generation molecules are described, usually of just first or second generation. The cascadepolymers have been synthesized starting either from a benzene ring, to which three cascade spheres are attached, or from alkyl halides with a single cascade sphere. More recently, arborols with a skeleton consisting of saturated hydrocarbon chains with external hydrophilic groups, have been developed. These macromolecules can host non-polar molecules in their lipophilic cavities and may thus be regarded as unimolecular micelles.

Polyether dendrimers (Ref. 13-19)

These derivatives have been synthesized by Fréchet and co-workers through an original synthetic approach involving two distinct steps:

a) preparing preformed dendrimeric fragments containing a reactive group, termed the "focal point";
b) assembling the dendrimeric molecule through reaction of the fragment focal points with the "core", which consists of a polyfunctional molecule.

However, by this approach the synthesis of dendrimers of fourth and higher generations is difficult because the reactivity of the focal point is reduced due to steric hindrance. The propagation monomers of these molecules are constituted by polyfunctional benzenes and thus these molecules are endowed with a certain degree of rigidity.

The first attempts at synthesizing branched molecules date back to 1978 when Buhleier, Wehner, and Vogtle. (Ref. 20) proposed a synthetic scheme that involved the frequent repetition of similar steps which would add successive branches to a starting molecule. In this way, compounds with increasingly growing cavity size were obtained. This process, termed "cascade-like" synthesis, used linear or cyclic mono or diamines as starting molecules which, by reaction with acrylonltrile followed by reduction, give rise to new branching points. Recently, other types of dendrimers have been synthesized. Miller et al. (Ref. 21) prepared a series of dendrimers, containing 4, 10, 22 or 46 benzene rings which possess symmetrical and rigid molecular structures. Such dendrimers are thermally stable and, with the exception of the sparingly soluble first generation, are soluble in organic solvents such as THF, toluene and chloroform. The author suggested the use of these products as standards for size-exclusion chromatography. Uchida et al. (Ref. 22) and Mathias and Carothers (Ref. 23) synthesized silicone-based dendrimers up to the third generation. However, for the dendrimers of Mathias and Carothers, the absolute molecular weight, molecular weight distribution and uniformity of branching are still unknown.

Dendrimers having charges within the cascade structure have been described by Rengan and Engel (Ref 24, 25). These are phosphonium or ammonium sites and only the first three generations have been synthesized. Morikawa et al. (Ref. 26) synthesized starburst dendrimers containing polysiloxane units up to the third generation whose potential applications could be as drug carriers. Nagasaki et al. (Ref. 27) described the synthesis of arborols with encapsulated crown ethers in the hope of producing compounds with novel physical properties such as the selectivity towards alkali metal ions, the allosteric effect in the metal-binding process, the conformational change induced by the metal-binding and the polyelectrolyte-like behaviour of the resulting metal complexes. However, none of these characteristics have so far been demonstrated. These dendrimers were synthesized by the convergent synthetic approach. Because of the insolubility of the first generation and the steric hindrance of functional groups on the molecule, the divergent approach was also examined but failed to give the desired molecules.

To date only the second generation has been obtained.

Polynuclear transition metal complexes of dendrimeric nature have been synthesized by Serroni et al. (Ref. 28).

Building repetition blocks are linked not only through covalent bonds but also through metal chelate bonds.

Brabander-van den Berg et al. (Ref. 30) synthesized poly(propylene imine) dendrimers up to the fifth generation. These dendrimers are obtained through repetitive double Michael addition of acrylonitrile to primary amines, followed by a heterogeneously catalyzed hydrogenation of the nitrites. These kinds of dendrimers are not sensitive to hydrolytic degradation and are stable at high temperature. The process by which they are prepared is suitable for large scale productions.

As already mentioned, dendrimers reported in the literature have been obtained by two different synthetic approaches:

a) divergent synthesis; b) convergent synthesis.

The syntheses of most dendrimers have been accomplished using the divergent process. This implies that a polyfunctional molecule is used as a "core" and that, in order to introduce multiplicity, each functional group is bonded to a molecule which also comprises more than one protected reactive site ("propagation monomer"). A first generation dendrimer is thus formed which, by exhaustive addition of polyfunctionalized monomers, gives rise to the next generation and so on. Monomer protection/deprotection systems need to be used in order to perform the selective modification of specific groups at each synthetic step.

Convergent synthesis, as first proposed by Fréchet, differs from the divergent approach in that growth starts at what will become the periphery of the macromolecule.

Such a method results in the formation of large dendrimeric fragments, which ultimately are attached through a reactive group ("focal point") to a polyfunctional "core".

Convergent synthesis has certain advantages over divergent synthesis. With divergent synthesis, the molecule's growth occurs through the simultaneous addition of an increasing number of reactive sites. With the convergent approach, on the other hand, size increase involves a limited number of reactive sites. Convergent synthesis makes use of a smaller excess of reagents. Possible side reactions are therefore avoided and the final products more easily purified.

However, one limitation of the convergent approach is that, as the size of the dendrimers increases, there is an increase in the steric hindrance near the functional group, or focal point, which prevents the group from reacting with the "core". This limitation is also common in divergent synthesis since the size of the molecule increases more slowly than the number of external functional groups. This leads to an increase in steric hindrance around the functional groups which are thus prevented from reacting to give the next generation.

There are notable differences among the different types of dendrimers. With regard to the starburst dendrimers, PAMAM and the polyethers possess different multiplicity of the "core" (3 for PAMAM; 4 for the polyethers); as a result PAMAM are much less sterically hindered than the polyethers and show internal cavities. These characteristics allow the synthesis of PAMAM products with higher generation numbers than is possible with polyethers for which the phenomenon of "dense-packing" is already apparent by the third generation. On the other hand, the early generations of PAMAM dendrimers, unlike the polyethers, do not have definite shapes; only the more advanced generations of PAMAM dendrimers have definite shapes. In addition, the large excess of reagents (typically ethylenediamine) that are required for the synthesis of PAMAM can cause problems.

In the early generations these reagents are easily removed.

However, as dendrimers grow, the removal of these excesses becomes more difficult. The same is true for certain by-products which may arise from incomplete Michael addition reactions, from intramolecular cyclizations, from fragmentation due to retro-Michael reactions or from intermolecular cyclizations that result in the formation of bridges between two dendrimers. These problems are not seen with starburst polyethers where an excess of reagents is not necessary and where the dendrimers are crystalline.

This makes the purification of polyether dendrimers much easier.

As regards L-lysine-based Denkewalter dendrimers, they have asymmetric "branches" and their structures have not been rigourously established. The different lengths of the "branches" can cause steric hindrance because a few functional groups are buried in the internal part of the molecule and therefore sterically hindered and unreactive.

Newkome et al. (Ref. 8-12, 29) have synthesized less branched, less sterically hindered molecules which have large lipophilic internal cavities capable of accepting hydrophobic molecules and which in solution behave similarly to micelles. The synthesis of such molecules is rather complex, because of the unreactivity of the neopentyl centre ("core") to nucleophilic reactions (Ref. 11). To overcome this drawback, the introduction of a "spacer" of at least 3 atoms was necessary.

The dendrimeric macromolecules described above have been synthesized with specific uses in mind. They could, for example, be used as transporters of high quantities of substances and it is for this reason that dendrimers are extensively studied as possible "carriers" for the controlled and targeted release of drugs. It is possible to prepare dendrimers with a lipophilic interior and a hydrophilic surface thus obtaining molecules that can function as micelles. Compared to micelles, such molecules, as a result of their intrinsic characteristics, could show much greater stability. By utilizing suitable monomers in the latter generation, it is theoretically possible to control the porosity of the external sphere of the molecule. In this regard, dendrimers can perhaps be compared with cells. Furthermore, these polymers are characterized by large surface areas which, in combination with high solubility in organic solvents, might facilitate their use as carriers of catalysts that could be recovered at the end of the reaction by simple extraction or filtration.

Compounds that are suitable for association with dendrimers are, in general, molecules that can be used either for therapeutic treatment or for in vivo or in vitro diagnosis. Compounds of this type are for example pharmaceuticals (such as antibiotics, analgesic, antihypertensives, and cardiotonics) used in the treatment of various diseases;

radionuclides; signal generators and absorbers; antibodies; metal chelates; opacifying diagnostics and hormones. The in vivo and in vitro diagnostic procedures which could benefit from the use of dendrimer derivatives are, for example: radioimmunologic assays, electron microscopy, ELISA, X-ray imaging, magnetic resonance imaging (MRI) and immunoscintigraphy. Dendrimers can also have other uses, for example as "carriers" of chemical substances for agriculture, as adhesives, as absorbents, as oil/water demulsifiers, as thickeners of plastic materials, as calibration standards for ultrafiltration membranes and electron microscopy, as standards for size-exclusion chromatography, and as agents to modify the Theological properties of solutions of dyes and paints. Despite all these possible applications, however, none as yet have been fully realised. This is in part due to the difficulties in synthesizing dendrimers with a large number of generations (because of the "dense-packing" problem), and in part because of the difficulties in the synthesis of three-dimensional structures with adequate internal cavities, in terms of number and dimension, for the intended use.

The objects of the present invention are new, dendrimeric-type macromolecules that comprise the following structural groups:

a) a central "core", derived from a polyvalent organic molecule from which at least two polyoxaalkyl chains originate, b) at least two polyoxaalkyl chains, preferably polyoxyethylene or polyoxypropylene, that are connected to the above-mentioned "core", c) at least two polyvalent branched organic residues attached to the ends of said chains which function as branching points for the subsequent growth of the molecule, because each of these points can be reacted with two or more reactive groups of other polyoxaalkyl chains, d) possibly further polyoxaalkyl chains and branching points added in succession until the molecule reaches the desired dimension.

One polyoxaalkyl chain, taken together with its branching point, constitutes a growth, or repetition unit. The total amount of growth units comprised in the same shell or growth level represents a generation.

"Core" and branching points are characterized by a multiplicity number which refers to either the number of functional groups on the "core", that enable growth of the molecule, or to the degree of branching possible at each branching point.

The introduction of the first branching point in the molecule determines the first generation, the introduction of a successive branching point determines the second generation and so on. The length of the polyoxaalkyl chain between the "core" and the first branching point, or between one branching point and the next one, can vary.

Such chain lengths are chosen according to the structure and the characteristics required for the macromolecule. For example, the chain length influences the formation of the internal cavities within the structure and/or the compactness (density) of the molecule, and in the early generations particularly, its geometric form as well. The polyoxyethylene chains, as a non-limiting example of polyoxaalkyl chains, are characterized by the $-[OCH_2CH_2]n-$ unit where n is a number from 0 to 25 and preferably from 0 to 15. It is therefore possible, when n=0, to have two branching points next to each other without a polyoxaalkyl chain separating them. Nevertheless, highly preferred compounds are those in which at least one of the generations include polyoxaalkyl chains in which n is different from 0. The distance between the "core" and the first branching point, or between one branching point and next one, is determined by the length of the polyoxaalkyl chain, i.e. by the value of n. This value can be equal in each generations or can vary from generation to generation.

The central nucleus of the compounds of the present invention can be derive from any polyvalent, aliphatic organic open chain residue, both branched and not, or from alicyclic residues, or from heterocyclic residues containing N, O and/or S, or from aromatic or heteroaromatic residues. All of them are substituted by at least two reactive groups to which the polyoxaalkyl chains of the first generation are covalently attached. The "core" can also possess one or more reactive groups that do not participate to the growth of the molecule but which are possibly available for the coupling to other structures or as dimerization points. Non-limiting examples of "core" include, among others, NH3, substituted amines, diamines, suitably functionalized aromatic rings, molecules with neopentyl centres (pentaerythritol, hydroxymethylpropantriol), and triaza- and tetraazamacrocycles. Branching points can consist of polyvalent residues with at least two or three reactive functions suitable for introducing multiplicity. In each dendrimer, the branching points can be the same in each generation or may vary from generation to generation.

Multiplicity can also be introduced for example using polyoxaalkyl chains in which the terminal part is already branched. The multiplicity of the "core", the multiplicity of the branching points and the value of n can be chosen according to the characteristics/properties desired in the final macromolecule. In this way it is possible to obtain macromolecules with different distributions of functional groups on the external surface: for example, zonal distribution if the polyoxaalkyl chains connected to the "core" are long and those of the branches short, or uniform distribution if the polyoxaalkyl chains are of equal length. In both cases there will be a different density of terminal groups and/or chains between the peripheral and the central part of the molecule. Increasing the branching multiplicity, with all other parameters equal, results in a notable increase of hindrance at the peripheral part of the structure, relative to the central part. With the degrees of freedom conferred by the length of the polyoxaalkyl chains, by the multiplicity of the "core" and the branching points, one can obtain macromolecules with internal cavities of different dimensions, which are either all equal or which vary from generation to generation.

A further advantage arising from the introduction of polyoxaalkyl chains between the "core" and the first branching point, or between one branching point and the next one, is that in this way it is possible to construct molecules that are able to grow further giving structures with a large number of generations. This is the fundamental point of the present invention. Additionally, it is also possible to avoid the phenomenon of "dense-packing", a phenomenon that severely hampers the preparation of the dendrimers of the prior-art by restricting the number of successive generations obtainable. As a general rule, one of the main obstacles to the synthesis of dendrimeric structures is the excessive surface area crowding that inevitably arises with higher numbers of generations. For this reason the growth of the structure becomes progressively more difficult; for example, preparation of molecules of the third generation, in the case of polythioethers, or of the fourth in the case of polyethers, is effectively impossible as reported by Tomalia (Ref. 1).

On the contrary the introduction of polyoxaalkyl chains enables the preparation of molecules with less compact structures. For these macromolecules, problems due to the inclusion of reagents and solvents during the various synthetic steps, phenomenon which can cause significant difficulty during the purification process, are very much reduced.

The external surfaces of the macromolecules of the present invention are well provided with functional groups such as for example hydroxyl, tosyl, mesyl, tresyl, brosyl and similar groups, trifluoromethanesulfonyl, phthalimido, amino, thiol, aldehydo, nitrilo, acetyl, pyranyl, cyclic orthoester, carboxyl and amido groups.

As a consequence, the compounds of the present invention may be ideally suited to the transport of drugs and/or molecules for use in diagnostic imaging. Both these classes of compounds can be linked to such macromolecules, either directly or through suitable spacer chains, alternatively they can be included in the macromolecules themselves.

Concerning diagnostic imaging, it is, for example, possible to obtain contrast agents for magnetic resonance (MRI) by linking paramagnetic metal chelates, such as chelates of polyaminopolycarboxylic acids, to these molecules. In this respect they could represent a good solution to the development of new effective blood-pool agents.

Ferromagnetic or superparamagnetic (ferrite, magnetites or derivatives thereof) compounds can also be included in the internal cavities of the macromolecules for diagnostic use in MRI.

The macromolecules of the present invention can also be linked to chelates of radioactive metal ions for use in nuclear medicine, or conjugated to iodinated molecules for use in all roentgenographic diagnostic investigations.

The molecules may also be labelled with isotopes such as $^{13}C$, $^{14}C$, $^{2}H$, $^{3}H$ or $^{125}I$ and used subsequently in biodistribution studies. Moreover, they may be used in the preparation of pharmaceutical products where controlled release of the active principle is required. Moreover, it is even possible to modify the external functional groups with suitable hydrophobic groups to create a molecular structure that behaves as an inverse micelle, i.e. with a hydrophilic internal part and a hydrophobic surface.

Moreover such macromolecules are highly promising as carriers of catalysts, allowing a complete recovery of the same after the reaction. Finally, since the macromolecules of the present invention can be prepared to precise and definite dimensions, they are particularly useful as calibration standards for separation techniques based on molecular shape, such as for example size-exclusion chromatography.

The compounds of the present invention are represented by the following general formula (I)

$$A[G_{1 \to p}]_r \qquad (I),$$

where:
- A is a central nucleus, or "core", deriving from a polyvalent organic molecule which can be an aliphatic open chain, branched or not, residue, or an alicyclic, or a heterocyclic residue containing N, O and/or S, or an aromatic or a heteroaromatic residue and which is characterized by the presence of r terminal residues to which the polyoxaalkyl chains of the first generation are attached.
- r is an integer from 2 to 10 representing the multiplicity of the "core" A.
- $G_{1 \to p}$ represents the branched structure of the macromolecule comprising g levels of generations, from the first one ($g_1$) to the last one ($g_p$) in which the total p number of said generations can range from 1 to 20 and in which the different generations can contain the same repetition units or not, and in which:

a) each generation g, except for the last, comprises a number of repetition units, which are represented by residues of formula

—B—M— where:

B is preferably a polyoxyethylene or polyoxypropylene chain of formula:

$$+O+CH_2\overline{)_{n-1}}CH_2-CH_2+_n$$

in which n can range from 0 to 25 and is different or not from generation to generation, provided that, in at least one of the generations of the macromolecule, n is different from 0, M represents a branching point which derives from a polyvalent aliphatic residue comprising:
- a single functional group such as OH, $NH_2$, SH, COOH, or a derivative thereof, able to link with the terminal group of chain B,
- m reactive residues for the linking of the polyoxaalkyl chains of the next generation, being m an integer ranging from 2 to 5, representing the branching multiplicity introduced by M and being m different or not from generation to generation, and being the total number of repetition units —B—M— in each generation level g equal to the sum of all the branching multiplicities m of the preceding generation $g_{-1}$;

b) the last generation gp comprises residues of formula:

—$B_p$—$M_p[T]_{m_p}$ where $B_p$, $M_p$, $m_p$ are defined analogously to B, M, and m, with the difference that all the $M_p$ reactive residues of $M_p$ are connected to groups T in which T is a terminal group that can be either H or one of the following residues: halo, hydroxyl, amino, thiol, —O-tosyl, —O-mesyl, —O-tresyl, —O-brosyl and similar groups, trifluoromethanesulfonyl, aldehydo, carboxy, amido group, such a terminal group T being free, either dissociated or undissociated, or protected by suitable protective groups such as for example, pyranyl, phthalimido, acetyl, cyclic orthoester group etc. and being the total number of the terminal groups r equal to the sum of all the branching multiplicities m of the last generation $g_p$, and with the further condition that $M_p$ can also be a single bond, in which case $m_p$ is equal to 1 (i.e., there is no branching) and as a consequence the last generation $g_p$ comprises residues of formula:
—$B_p$—T where $B_p$ and T are as above defined;

c) in case p=1, that is when the macromolecule contains only one generation, $g_p$ corresponds to $g_1$, i.e. represents the residue:

—$B_1$—$M_1[T]_{m_1}$ where $B_1$, $M_1$, $m_1$ and T are defined analogously to $B_p$, $M_p$, $m_p$ and T.

As a consequence, in this case the macromolecule is represented by the following formula $A|g_1|_r$ i.e.

$A|B_1-M_1|T|_{m_1}|_r$ in which A, $B_1$, $M_1$, T, $m_1$ and r are defined as above.

Compounds of general formula (I) also comprise those ones which are labelled with isotopes such as $^{13}C$, $^{14}C$, $^2H$, $^3H$, and $^{125}I$.

For seek of clarity a schematic representation of the structure of the macromolecules of the present invention is sequentially developed according to the following series of formulae:

$A|G_{1 \to p}|_r$ (I), where:

$G_{1 \to p}$ represents $B_1-M_1|G_{2 \to p}|m_1$, in which $B_1-M_1$ is $g_1$ and $G_{2 \to p}$ represents $B_2-M_2|G_{3 \to p}|m_2$, in which $B_2-M_2$ is $g_2$ and so on until the last generation is reached in which $G_p$ represents $B_p-M_p|T|_{mp}$, where the symbols used are as above defined.

The afore-mentioned development can be illustrated in complete form by the following expanded general formula (II)

$A|B_1-M_1|B_2-M_2|\to\to\to|B_p-M_p|T|_{mp}|\to\to\to|_{m2}|_{m1}|_r$ (II)

Compounds of the present invention which are particularly preferred are those in which r ranges from 2 to 6, preferably from 2 to 4 and in which the "core" A is a neopentyl residue of formula $C(CH_2\cdotp)_4$ Equally preferred are those in which B is a polyoxyethylene chain of formula $+O-CH_2-CH_2+_n$ in which n is an integer from 0 to 25, preferably from 0 to 15.

Also preferred are those in which M is a bi- or trifunctional branching point represented by a residue of formula:

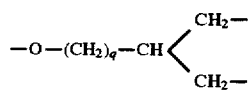

or

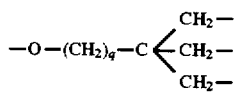

in which q is an integer from 0 to 4, preferably from 1 to 2.

Preferred macromolecular compounds are those in which the total number of generations ranges from 1 to 20, preferably from 1 to 15.

As an example of the invention one of the preferred classes of compounds is represented by those having the following general formula (III)

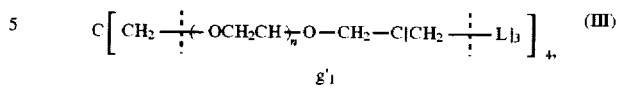

in which:

n is an integer from 0 to 20, preferably from 0 to 15, and with the condition that n is different from 0 in at least one generation, $g'_1$ is the first generation having a branching multiplicity of 3, L represents T, or the sequence of successive generations from $g'_2$ to $g'_p$, in which each $g'$, apart from $g'_p$, is defined analogously to $g'_1$ and can have the same meaning or not whereas $g'_p$ corresponds to $g'_1$-T and T is as above defined; moreover the number of generations g can be as high as 20, preferably 15.

The present invention is illustrated particularly through the preparation of branched macromolecules having a neopentyl "core" from which four polyoxyethylene chains depart. The branching is obtained through the introduction of a residue of pentaerythritol on the terminal residue of the polyoxyethylene chains. The synthesis of the compounds of the present invention can preferably be performed by two independent synthetic processes:

a) lengthening of the polyoxyethylene chain, b) branching.

The order of these synthetic pathways can be modulated at will, in particular with regard to the type of compound and reaction conditions employed. It is possible to decide to begin with the central nucleus and add successively the polyoxaalkyl chains of the first generation, the branching points, the polyoxaalkyl chains of the second generation, the new branching points and so on until the desired number of generations has been reached.

Alternatively, it is equally possible to prepare already branched polyoxaalkyl chains and then to attach these to either the central nucleus or to a previously formed generation.

Obviously, just as it is possible to utilize one or the other of the two synthetic processes, it is also possible to follow in part the first process and in part the second one according to the synthetic problem to overcome. The reactive functions not involved in a specific reaction are protected with suitable protective groups according to methods well known in chemical syntheses. A consequence of this is that also the process of preparation of these macromolecular compounds forms an embodiment of the present invention.

An illustrative view of the preferred synthetic pathways is given in the experimental part below.

Obviously, the experimental part only has the aim of exemplifying the invention more completely. Consequently, it is not absolutely limiting of the invention itself and any possible change that can be produced in the described examples is immediately evident to the expert technician.

EXAMPLE 1

Preparation of chlorooxyethylene chains with hydroxyl functions protected by dihydropyran 3,4-Dihydro-2H-pyran (0.6 mol) was slowly added dropwise into the desired chloroalcohol (0.5 mol) of Table II under magnetic stirring. The reaction temperature reached 100°–150° C. After allowing to cool to room temperature, the mixture was stirred for 2 h. The mixture was distilled under high vacuum to obtain the desired product as a colourless oil. By this synthetic pathway the following products were obtained:

AI 2-(3-chloroethoxy)oxane ($C_7H_{13}ClO_2$)
AII 2-(3-oxa-5-chloropentyloxy)oxane ($C_9H_{17}ClO_3$)
AIII 2-(3,6-dioxa-8-chlorooctyloxy)oxane ($C_{11}H_{21}ClO_4$)

The reaction yields and starting materials are summarised in Table II. Table III reports the analytical characterizations.

TABLE II

Synthesis of protected oxyethylene chains

| Product | Starting chloroalcohol | Reaction yield |
|---|---|---|
| AI | $ClCH_2CH_2OH$ | 85% |
| AII | $ClCH_2CH_2OCH_2CH_2OH$ | 91% |
| AIII | $ClCH_2CH_2OCH_2CH_2OCH_2CH_2OH$ | 80% |

TABLE III

Analytical characterization[a]

| Product | b.p. (pressure) | Elemental analysis | |
|---|---|---|---|
| AI | 100° C. (2676 Pa) | Calculated for $C_7H_{13}ClO_2$: | C 51.11; H 7.96 |
| | | found: | C 51.21; H 7.74 |
| AII | 85° C. (60 Pa) | Calculated for $C_9H_{17}ClO_3$: | C 51.80; H 8.21 |
| | | found: | C 51.64; H 8.16 |
| AIII | 125° C. (60 Pa) | Calculated for $C_{11}H_{21}ClO_4$: | C 51.80; H 8.40 |
| | | found: | C 51.49; H 8.44 |

$^1$H-NMR and $^{13}$C-NMR spectra of the described products are in agreement with the proposed structures.

Similar results were obtained when, in place of the above-mentioned monofunctional chloroalcohols, the bifunctional chloroalcohols, $ClCH_2—CH(CH_2OH)_2$ and $ClCH_2—CH_2—O—CH_2—CH(CH_2OH)_2$, were protected by pyranyl groups.

EXAMPLE 2

Alkylation By Phase Transfer Catalysis of Neopentyl "Core" Molecules With Protected Oxyethylene Chains The starting tetraalcohol (0.0156 mol) (Table IV) was dissolved in 19.06M NaOH (0.624 mol). The reaction mixture was than warmed to 65° C. under nitrogen and mechanically stirred. Tetrabutylammonium bromide (0.0062 mol) and the desired chlorooxyethylenepyranyl derivative (0.0936 mol) of Table IV, obtained according to the method of Example 1, were then added to this solution. The reaction mixture was incubated at 65° C. for 48 h. After this time a freshly prepared 19.06M NaOH solution (0.312 mol), the chlorooxyethylenepyranyl derivative (0.062 mol), tetraoctylammoniumbromide (0.0062 mol) and NaI (0.0036 mol) were added. The reaction mixture was stirred for an additional 66 h at 65° C. Tetraethylammonium hydroxyde solution (10 mL; 10% w/w in water) was then added and the mixture stirred for 48 h at 80° C. Finally the reaction was cooled to room temperature, diluted with $H_2O$ and the product extracted several times with diethylether. The organic layers were combined and dried over $Na_2SO_4$, filtered and concentrated under reduced pressure. The crude product thus obtained was subjected to fractional distillation and then chromatographed on a silica gel column (flash chromatography, eluent AcOEt). By this synthetic pathway the following were obtained:

BI 1,4,7,11,14,17-hexaoxa-1,17-bis(oxan-2-yl)-9,9-bis|2,5,8-trioxa-8-oxan-2-yl)octyl|heptadecane ($C_{41}H_{76}O_{16}$);

BII,III 1,4,7,10,14,17,20,23-octaoxa-1,23-bis(oxan-2-yl)-12,12-bis|2,5,8,11-tetraoxa-11-(oxan-2-yl)-undecyl| tricosane ($C_{49}H_{92}O_{20}$);

BIV,V 1,4,7,10,13,17,20,23,26,29-decaoxa-1,29-bis(oxan-2-yl)-15,15-bis|2,5,8,11,14-pentaoxa-14-(oxan-2-yl) tetradecyl|nonacosane ($C_{57}H_{108}O_{24}$).

The reaction yields and starting materials are summarised in Table IV. Table V reports the analytical characterizations.

TABLE IV

Alkylation reactions by phase transfer catalysis

| Product | Starting chlorooxyethylenepyran compound | Starting tetraalcohol | Reaction yield |
|---|---|---|---|
| BI | 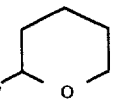 AII | $C(CH_2OH)_4$ | 54% |
| BII[a] | 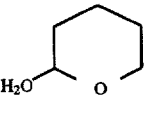 AIII | $C(CH_2OH)_4$ | 20% |
| BIII[a] | 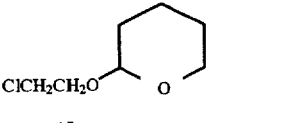 AI | $C(CH_2OCH_2CH_2OCH_2CH_2OH)_4$ CI | 50% |
| BIV[b] | 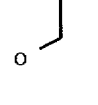 AI | $C(CH_2OCH_2CH_2OCH_2CH_2OCH_2CH_2OH)_4$ CII | 42% |

TABLE IV-continued

| Alkylation reactions by phase transfer catalysis | | | |
|---|---|---|---|
| Product | Starting chlorooxyethylenepyran compound | Starting tetraalcohol | Reaction yield |
| BV[b] | 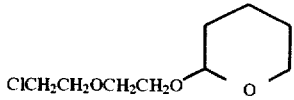 ClCH$_2$CH$_2$OCH$_2$CH$_2$O—[pyran] AII | C(CH$_2$OCH$_2$CH$_2$OCH$_2$CH$_2$OH)$_4$ CI | 39% |

[a]BII and BIII are the same product but synthetized from different starting materials.
[b]BIV and BV are the same product but synthetized from different starting materials.

TABLE V

| Analytical characterization[a] | | |
|---|---|---|
| Product | Elemental analysis | |
| BI | Calculated for C$_{41}$H$_{76}$O$_{16}$: found: | C 59.69; H 9.29 C 59.60; H 9.28 |
| BII | Calculated for C$_{49}$H$_{92}$O$_{20}$ · 0.7 mol H$_2$O: found: | C 58.08; H 9.23 C 58.16; H 9.30 |
| BIII | Calculated for C$_{49}$H$_{92}$O$_{20}$: found: | C 58.78; H 9.26 C 58.71; H 9.30 |
| BIV | Calculated for C$_{57}$H$_{108}$O$_{24}$ · 0.5 mol H$_2$O: found: | C 57.66; H 9.25 C 57.29; H 9.26 |
| BV | Calculated for C$_{57}$H$_{108}$O$_{24}$ · 0,6 mol H$_2$O: found: | C 57.66; H 9.25 C 57.49; H 9.37 |

[a]$^1$H-NMR and $^{13}$C-NMR spectra of the described products are in agreement with the proposed structures.

EXAMPLE 3
Deprotection Reaction of the Pyranyl Derivatives

The desired tetraoxyethylenepyranyl derivative (0.0024 mol) (Table VI), obtained according to the method of Example 2, was dissolved in a mixture of CH$_2$Cl$_2$/MeOH 1/1 (v/v) (20 mL). 37% HCl (0.5+0.8 mL) was added and the reaction mixture was stirred for 7 h at room temperature.

Subsequently, NaHCO$_3$ was added to neutral pH, the inorganic salts were filtered off and the organic layer dried over Na$_2$SO$_4$. The solvent was then removed under vacuum. The crude product was chromatographed on a silica gel column (eluent CH$_2$Cl$_2$/MeOH=85/15 (v/v)). By this synthetic pathway the following compounds were obtained:

CI 3,6,10,13-tetraoxa-8,8-bis-(2,5-dioxa-7-hydroxyheptyl) pentadecan-1,15-diol (C$_{21}$H$_{44}$O$_{12}$);

CII 3,6,10,13,16,19-hexaoxa-11,11-bis(2,5,8-trioxa-10-hydroxydecyl)enicosan-1,21-diol (C$_{29}$H$_{60}$O$_{16}$);

CIII 14,14-bis(2,5,8,11-tetraoxa-13-hydroxydecyl)-3,6,9,12,16,19,22,25-octaoxaheptacosan-1,27-diol (C$_{37}$H$_{76}$O$_{20}$)

The reaction yields and starting materials are summarised in Table VI. Table VII reports the analytical characterizations.

TABLE VI

| Deprotection reactions | | |
|---|---|---|
| Product | Starting tetraoxyethylenepyranyl | Reaction yield |
| CI | C(CH$_2$OCH$_2$CH$_2$OCH$_2$CH$_2$O—[pyran])$_4$ BI | 92% |
| CII | C(CH$_2$OCH$_2$CH$_2$OCH$_2$CH$_2$OCH$_2$CH$_2$O—[pyran])$_4$ BII | 90% |
| CIII | C(CH$_2$OCH$_2$CH$_2$OCH$_2$CH$_2$OCH$_2$CH$_2$OCH$_2$CH$_2$O—[pyran])$_4$ BIV | 93% |

TABLE VII

Analytical characterization[a]

| Product | Elemental analysis | |
|---|---|---|
| CI | Calculated for $C_{21}H_{44}O_{12} \cdot 2.25$ mol $H_2O$: | C 47.67; H 9.24 |
| | found: | C 47.33; H 9.15 |
| CII | Calculated for $C_{29}H_{60}O_{16} \cdot 1$ mol $H_2O$: | C 51.01; H 9.15 |
| | found: | C 50.76; H 9.31 |
| CIII | Calculated for $C_{37}H_{76}O_{20} \cdot 1.25$ mol $H_2O$: | C 51.46; H 9.10 |
| | found: | C 51.36; H 9.24 |

[a] $^1$H-NMR and $^{13}$C-NMR spectra of the described products are in agreement with the proposed structures.

EXAMPLE 4
Tosylation of the Tetraoxyethylenealcohols

The desired tetraoxyethylenealcohol (0.0102 mol) (Table VIII), obtained according to the method of Example 3, was dissolved in $CH_2Cl_2$. Triethylamine (0.123 mol) was added and the solution cooled to $-5°$ C. A solution of p-toluenesulfonyl chloride (0.0445 mol) in $CH_2Cl_2$ was then added dropwise. The mixture was stirred for an additional 1 h at 0° C. and then left at room temperature for 24 h. The mixture was washed with water and the organic layer separated and dried over $Na_2SO_4$. The solvent was then removed under vacuum. The crude product was purified by chromatography on a silica gel column (eluent $CHCl_3$/AcOEt 1/1 (v/v)). By this synthetic pathway the following compounds were obtained:

DI 1,4,7,11,14,17-hexaoxa-1,17-bis(p-toluensulfonyl)-9,9-bis|2,5,8-trioxa-8-(p-toluenesulfonyl)octyl|heptadecane ($C_{49}H_{68}O_{20}S_4$)

DII 1,4,7,10,14,17,20,23-octaoxa-1,23-bis(p-toluenesulfonyl)-12,12-bis|2,5,8,11-tetraoxa-11-(p-toluenesulfonyl)undecil|tricosane ($C_{57}H_{84}O_{24}S_4$)

DIII 15,15-bis|2,5,8,11,14-pentaoxa-14-(p-toluenesulfonyl)tetradecyl|-1,29-bis(p-toluensulfonyl)-1,4,7,10,13,17,20,23,26,29-decaosanonacosane ($C_{65}H_{100}O_{28}S_4$)

The reaction yields and starting materials are summarised in Table VIII. Table IX reports the analytical characterizations.

TABLE VIII

Tosylation reactions of the tetraoxyethylenealcohols

| Product | Starting tetraoxyethylenealcohol | Reaction yield |
|---|---|---|
| DI | $C(CH_2OCH_2CH_2OCH_2CH_2OH)_4$<br>CI | 75% |
| DII | $C(CH_2OCH_2CH_2OCH_2CH_2OCH_2CH_2OH)_4$<br>CII | 65% |
| DIII | $C(CH_2OCH_2CH_2OCH_2CH_2OCH_2CH_2OCH_2CH_2OH)_4$ | 60% |

TABLE VIII-continued

Tosylation reactions of the tetraoxyethylenealcohols

| Product | Starting tetraoxyethylenealcohol | Reaction yield |
|---|---|---|
| CIII | | |

TABLE IX

Analytical characterization[a]

| Product | Elemental analysis | |
|---|---|---|
| DI | Calculated for $C_{49}H_{68}O_{20}S_4 \cdot 0.5$ mol $H_2O$: | C 58.84; H 6.24; S 11.52 |
| | found: | C 52.46; H 6.26; S 11.40 |
| DII | Calculated for $C_{57}H_{84}O_{24}S_4$: | C 53.42; H 6.61; S 10 |
| | found: | C 53.65; H 7.00; S 10.14 |
| DIII | Calculated for $C_{65}H_{100}O_{28}S_4$: | C 53.55; H 6.91; S 8.80 |
| | found: | C 53.38; H 6.93; S 8.68 |

[a] $^1$H-NMR and $^{13}$C-NMR spectra of the described products are in agreement with the proposed structures.

In another tosylation experiment at kg scale, the reaction yield for DI was improved to 90% by inverting the addition order of the reagents and by keeping the reaction temperature at 0° C.

EXAMPLE 5
Reaction of the Tosyl Derivatives With Potassium Phthalimide thee desired tetraoxyethylenetosyl derivative (0.0018 mol) (Table X), obtained according to the method of Example 4, was dissolved in DMF. Potassium phthalimide (0.0072 mol) suspended in DMF was then added to the solution. After 7 h at 140° C. the reaction mixture was cooled to room temperature. The DMF was then removed under vacuum and $H_2O$ added to the residue. The reaction mixture was taken up and extracted with $CH_2Cl_2$. The organic layer was dried over $Na_2SC)_4$, filtered and the solvent removed under vacuum. The crude product was chromatographed on a silica gel column (flash chromatography; eluent $AcOEt/CHCl_3=7/3$ (v/v)). By this synthetic pathway the following compounds were obtained:

EI 3,6,10,13-tetraoxa-1,15-bis(phthalimido)-8,8-bis|2,5-dioxa-7-(phthalimido)heptyl| pentadecane ($C_{53}H_{56}N_4O_{16}$)

EII 3,6,9,13,16,19-hexaoxa-1,21-bis(phthalimido)-11,11-bis|2,5,8-trioxa-10-(phthalimido) decyl|enicosane ($C_{61}H_{72}N_4O_{20}$)

The reaction yields and starting materials are summarised in Table X. Table XI reports the analytical characterizations.

TABLE X

Reaction with potassium phthalimide

| Product | Starting tetraoxyethylenetosyl derivative | Reaction yield |
|---|---|---|
| EI | $C\left(CH_2OCH_2CH_2OCH_2CH_2OSO_2-\langle C_6H_4\rangle-CH_3\right)_4$ DI | 85% |
| EII | $C\left(CH_2OCH_2CH_2OCH_2CH_2OCH_2CH_2OSO_2-\langle C_6H_4\rangle-CH_3\right)_4$ DII | 65% |

TABLE XI

Analytical characterization[a]

| Product | Elemental analysis | |
|---|---|---|
| EI | Calculated for $C_{53}H_{56}N_4O_{16}$ · 1 mol $H_2O$: | C 62.20; H 5.52; N 5.47 |
| | found: | C 62.55; H 5.71; N 5.44 |
| EII | Calculated for $C_{61}H_{72}N_4O_{20}$: | C 62.02; H 6.14; N 4.74 |
| | found: | C 61.65; H 6.22; N 4.6 |

[a]$^1$H-NMR and $^{13}$C-NMR spectra of the described products are in agreement with the proposed structures.

EXAMPLE 6

Conversion of the Phthalimido Derivative into the Corresponding Tetraoxyethyleneamino Derivative The tetraoxyethylenephthalimido derivative EI (0.00199 mol) (Table XII), obtained according to the method of Example 5, was suspended in absolute ethanol. A solution of hydrazine (0.0119 mol) in absolute ethanol was then added otherwise. The reaction mixture was refluxed for 7 h and then cooled to room temperature. A precipitate was formed and filtered and the solvent removed under vacuum to give the final product. By this synthetic pathway the following compound was obtained:

FI 3,6,10,13-tetraoxa-8,8-bis(2,5-dioxa-7-aminoheptyl) pentadecan-1,15-diamine ($C_{21}H_{48}N_4O_8$)

The reaction yield and the starting material are summarised in Table XII. Table XIII reports the analytical characterizations.

TABLE XII

Conversion of the phthalimido derivative into the tetraoxyethyleneamino derivative

| Product | Starting tetraoxyethylenephthalimido derivative | Reaction yield |
|---|---|---|
| FI | $C\left(CH_2OCH_2CH_2OCH_2CH_2N(CO)_2C_6H_4\right)_4$ EI | 70% |

TABLE XIII

Analytical characterization[a]

| Product | Elemental analysis | |
|---|---|---|
| FI | Calculated for $C_{21}H_{48}N_4O_8$ · 3 mol $H_2O$: | C 46.96; H 10.14; N 10.43 |
| | found: | C 46.83; H 9.96; N 10.03 |

[a]$^1$H-NMR and $^{13}$C-NMR spectra of the described products are in agreement with the proposed structures.

EXAMPLE 7

Conversion of the Tosyl Derivative into the Corresponding Tetraoxyethylenebromide Derivative The tetraoxyethylenetosyl derivative DI (0.00325 mol) (Table XIV), obtained according to the method of Example 4, was dissolved in N,N-dimethylacetamide. NaBr (0.026 mol) was added and the reaction mixture stirred for 1 h at 150° C. The mixture was then cooled to room temperature and the solvent removed under vacuum. The residue was taken up into water and extracted with AcOEt. The organic layer was dried over $Na_2SO_4$, filtered and the solvent removed under vacuum. The crude product was purified by chromatography on a silica gel column (eluent AcOEt/ $CHCl_3$ 1/1 (v/v)). By this synthetic pathway the following compound was obtained:

GI 3,6,10,13-tetraoxa-8,8-bis(2,5-dioxa-7-bromoheptyl) pentadecan-1,15-dibromide ($C_{21}H_{40}O_8Br_4$)

The reaction yield and starting material are summarised in Table XIV. Table XV reports the analytical characterization.

TABLE XIV

Conversion of the tosylderivative into the tetraoxyethylenebromide derivative

| Product | Starting tetraoxyethylenetosyl derivative | Reaction yield |
|---|---|---|
| GI | C(CH₂OCH₂CH₂OCH₂CH₂OSO₂—⟨C₆H₄⟩—CH₃)₄  DI | 60% |

TABLE XV

Analytical characterization[a]

| Product | Elemental Analysis | |
|---|---|---|
| GI | Calculated for $C_{21}H_{40}O_8Br_4 \cdot 3$ mol $H_2O$: | C 34.08; H 5.45; Br 43.18 |
| | found: | C 34.20; H 5.47; Br 43.04 |

[a] $^1$H-NMR and $^{13}$C-NMR spectra of the described products are in agreement with the proposed structures.

EXAMPLE 8

Branching of the Oxyethylene Chains by Reaction With Compounds Having Further Functional Groups For Subsequent Alkylation (Example of Introduction of a Branching Point With Multiplicity=3)

4-(Hydroxymethyl)-2,6,7-trioxabicyclo[2.2.2]octane (0.00452 mol), prepared according to the method described by Padias et al. (Ref. 5), was dissolved in diethyleneglycol dimethylether (15 mL) and then added dropwise at 0° C. to a solution containing a stoichometric quantity of potassium hydride. The reaction mixture was stirred for 1 h at 0° C. and then for 3 h at room temperature. The desired tetraoxyethylenetosyl derivative (0.001808 mol) (Table XVI), obtained according to the method of Example 4, and dissolved in diethyleneglycol dimethylether (25 mL) was then added dropwise to the solution. The reaction mixture was then stirred at 120° C. for 14 h. After cooling to room temperature, the solvent was removed under vacuum and the mixture taken up with water and extracted with $CH_2Cl_2$. The organic layer was dried over $Na_2SO_4$, filtered and the solvent removed under vacuum. The crude product was purified by chromatography on a silica gel column (eluent AcOEt). The fractions containing the product were combined and the solvent removed under vacuum. The residue was dissolved in MeOH and then 37% HCl was added. The mixture was refluxed and the MeOH distilled off very slowly over a period of 2 h. The mixture was cooled to room temperature and the remaining MeOH removed under vacuum. The product was then obtained as a colourless oil. By this synthetic pathway the following compounds were obtained:

HI 4,7,10,14,17,20-hexaoxa-2,2,22,22-tetra(hydroxymethyl)-12,12-bis|2,5,8-trioxa-10,10-bis(hydroxymethyl)-11-hydroxyundecyl|tricosan-1,23-diol ($C_{41}H_{84}O_{24}$)

HII 18,18-bis|2,5,8,11,14-pentaoxa-16,16-bis(hydroxymethyl)-17-hydroxyheptadecyl|-2,2,34,34-tetra(hydroxymethyl)-4,7,10,13,16,20,23,26,29,32-decaoxapentatriacontan-1,35-diol ($C_{57}H_{116}O_{32}$)

The reaction yield and starting material are summarised in Table XVI. Table XVII reports the analytical characterization.

TABLE XVI

Branching reactions

| Product | Branching junction | Tetraoxyethylenetosyl derivative | Reaction yield |
|---|---|---|---|
| HI | C(CH₂OH)₄ | C(CH₂OCH₂CH₂OCH₂CH₂OSO₂—⟨C₆H₄⟩—CH₃)₄  DI | 35% |
| HII | C(CH₂OH)₄ | C(CH₂OCH₂CH₂OCH₂CH₂OCH₂CH₂OSO₂—⟨C₆H₄⟩—CH₃)₄  DIII | 29% |

TABLE XVII

Analytical characterization[a]

| Product | Elemental analysis | |
|---|---|---|
| HI | Calculated for $C_{41}H_{84}O_{24} \cdot 2.5$ mol $H_2O$: | C 50.38; H 8.87 |
| | found: | C 50.25; H 9.02 |
| HII | Calculated for $C_{57}H_{116}O_{32} \cdot 2.5$ mol $H_2O$: | C 50.29; H 8.98 |
| | found: | C 50.37; H 8.98 |

[a] $^1$H-NMR and $^{13}$C-NMR spectra of the described products are in agreement with the proposed structures.

EXAMPLE 9

Tosylation Reaction of Branched Alcohols Derivatives

The branched alcohol HI (0.00208 mol) (Table XVIII), obtained according to the method of Example 8, was dissolved in pyridine (40 mL) and the solution cooled to −5° C. A solution of p-toluenesulfonyl chloride (0.00583 mol) in pyridine (50 mL) was then added dropwise. The mixture was stirred for 1 h at 0° C. and then left at room temperature for 4 days. Water was added and the mixture extracted with CHCl3. The organic layer was dried over $Na_2SO_4$ and then the solvent was removed under vacuum. The crude product was purified by chromatography on a silica gel column (eluent AcOEt/$CHCl_3$ 1/1 (v/v)). By this synthetic pathway the following compound was obtained:

LI  1,23-di(p-toluenesulfonyloxy)-12,12-bis|11-(p-toluenesulfonyloxy)-10,10-bis(p-toluenesulfonyloxymethyl)-2,5,8-trioxaundecyl|-2,2,22,22-tetra(p-toluenesulfonyloxymethyl)-4,7,10,14,17,20-hexaoxatricosane ($C_{125}H_{156}O_{48}S_{12}$)

The reaction yield and starting material are summarised in Table XVIII. Table XIX reports the analytical characterization.

TABLE XVIII

Tosylation of the branched alcohol

| Product | Starting branched alcohol | Reaction yield |
|---|---|---|
| LI | $C[CH_2OCH_2CH_2OCH_2CH_2OCH_2C(CH_2OH)_3]_4$<br>HI | 50% |

TABLE XIX

Analytical characterization[a]

| Product | Elemental analysis | |
|---|---|---|
| LI | Calculated for $C_{125}H_{156}O_{48}S_{12}$ · 1 mol $H_2O$: | C 53.40; H 5.59; S 13.69 |
| | found: | C 53.78; H 5.86; S 13.35 |

[a] $^1$H-NMR and $^{13}$C-NMR spectra of the described products are in agreement with the proposed structures.

EXAMPLE 10
Conversion of the Branched Tosyl Derivatives into the Corresponding Bromo Derivatives The tosyl derivative LI (0.00051 mol) (Table XX), obtained according to the method of Example 9, was dissolved in N,N-dimethylacetamide (50 mL). NaBr (0.01224 mol) was added and the reaction mixture stirred for 1 h at 150° C. The temperature was then cooled to room temperature and the solvent removed under vacuum. The residue was taken up with water and extracted with $CH_2Cl_2$. The organic layer was dried over $Na_2SO_4$ and the solvent removed under vacuum.

The crude product was purified by chromatography on a silica gel column (eluent AcOEt/$CHCl_3$ 1/2 (v/v)). By this synthetic pathway the following compound was obtained:

MI  1,23-dibromo-12,12-bis|11-bromo-10,10-bis(dibromomethyl)-2,5,8-trioxaundecyl|-2,2,22,22-tetrabromomethyl-4,7,10,14,17,20-exaoxatricosane ($C_{41}H_{72}O_{12}Br_{12}$)

The reaction yield and starting material are summarised in Table XX. Table XXI reports the analytical characterization.

TABLE XX

Conversion into bromo derivative

| Product | Branched tosyl derivation | Reaction yield |
|---|---|---|
| MI | $C[CH_2OCH_2CH_2OCH_2CH_2OCH_2C(CH_2OSO_2\text{-}C_6H_4\text{-}CH_3)_3]_4$<br>LI | 67% |

TABLE XXI

Analytical characterization[a]

| Product | Elemental analysis | |
|---|---|---|
| MI | Calculated for $C_{41}H_{72}O_{12}Br_{12}$: | C 28.7; H 4.23; Br 55.88 |
| | found: | C 28.93; H 4.33; Br 55.65 |

[a] $^1$H-NMR and $^{13}$C-NMR spectra of the described products are in agreement with the proposed structures.

EXAMPLE 11
Introduction of Polyoxyethylene Chains on Molecules With Branched Alcohol Terminal Groups The branched alcohol HI (0.00104 mol) (Table XXII), obtained according to the method of Example 8, was dissolved in 19.06M NaOH (0.125 mol) under nitrogen. The reaction mixture was warmed up to 65° C. under mechanical stirring. Tetrabutylammonium bromide (0.00042 mol) and the chlorooxyethylenepyranyl derivative (0.00187 mol) were then added. The reaction mixture was incubated at 65° C. for 72 h.

Freshly prepared 19.06M NaOH solution (0.125 mol), the chlorooxyethylenepyranyl derivative (0.0125 mol), tetraoctylammonium bromide (0.000104 mol) and NaI (0.00005 mol) were added and the reaction was stirred for 72 h at 65° C. Tetraethylammonium hydroxide solution (5 mL; 10% w/w in water) was added and the mixture stirred for 96 h at 80° C. Finally the reaction was cooled to room temperature, diluted with water and extracted with $CHCl_3$. The organic layer was dried over $Na_2SO_4$, filtered and concentrated under reduced pressure. The crude product was chromatographed on a silica gel column. The by-products were eluted with AcOEt and the compound of interest was eluted with a mixture of AcOEt/Acetone 7/3 (v/v). By this synthetic pathway the following compound was obtained:

NI  1,35-di(oxan-2-yl-oxy)-18,18-bis|17-(oxan-2-yl-oxy)-10,10-bis(7-(oxan-2-yl-oxy)-2,5-dioxaheptyl)-2,5,8,12,15-pentaoxaheptadecyl|-8,8,28,28-tetra|(7-oxan-2-yl-oxy)-2,5-dioxaheptyl|3,6,10,13,16,20,23,26,30,33-decaoxapentatricontane ($C_{149}H_{276}O_{60}$)

The reaction yield and starting material are summarised in Table XXII. Table XXIII reports the analytical characterization.

TABLE XXII

Introduction of protected oxyethylene chain

| Product | Starting alcohol | Pyranyl derivative | Reaction yield |
|---------|------------------|--------------------|----|
| NI | $C[CH_2OCH_2CH_2OCH_2CH_2OCH_2C(CH_2OH)_3]_4$ HI | $ClCH_2CH_2OCH_2CH_2O$-pyranyl AII | 40% |

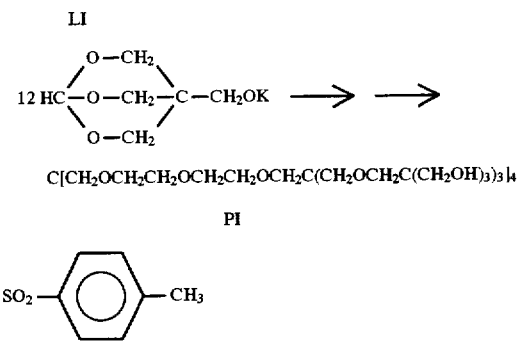

TABLE XXIII

Analytical characterization[a]

| Product | Elemental analysis | | |
|---------|---------------------|---|---|
| NI | Calculated for $C_{149}H_{276}O_{60}$ · 0.5 mol $H_2O$: | C 58.94; H 9.19; O 31.87 | |
| | found: | C 58.57; H 9.32; O 32.14 | |

[a] $^1$H-NMR and $^{13}$C-NMR spectra of the described products are in agreement with the proposed structures.

The same product was also obtained with a similar synthetic procedure using only tetrabutylammonium hydrogen sulfate as catalyst. Following such a procedure, the reaction yield was improved to 55%. The reaction yield for the introduction of twelve oxyethylene chains was surprisingly high being at least equal or even superior to those observed for the introduction of four oxyethylene chains as described in Example 2. This unexpected feature suggests that these compounds play a role in the phase-transfer catalysis.

Similar results were obtained when the described reaction was carried out on branched molecules with multiplicity=2, or when monochlorodipyranyl derivatives such as those described in Example 1 were utilized as lengthening units.

EXAMPLE 12

Introduction of a Further Branching Point (Multiplicity=3)

a) The second generation was obtained according to the method described in Example 8 by reacting the dodecatosyl derivative LI, obtained according to the method described in Example 9, with a stoichometric quantity of the potassium salt of 4-(hydroxymethyl)-2,6,7-trioxabicyclo[2.2.2]octane.

Reaction scheme:
$C[CH_2OCH_2CH_2OCH_2CH_2OCH_2C(CH_2OTs)_3]_4$ +

LI $12\ HC\begin{pmatrix}O-CH_2\\O-CH_2\\O-CH_2\end{pmatrix}C-CH_2OK \longrightarrow \longrightarrow$ $C[CH_2OCH_2CH_2OCH_2CH_2OCH_2C(CH_2OCH_2C(CH_2OH)_3)_3]_4$

PI $Ts = -SO_2-\text{C}_6\text{H}_4-CH_3$

Yield: 19%.

$^1$H-NMR, $^{13}$C-NMR and mass spectra of all the products described are in agreement with the proposed structure. The same product can be synthesized by starting from the dodecabromo derivative (MI), obtained using the method described in Example 10, by using the same synthetic approach of this example.

b) The compound NI, obtained according to the method described in Example 11, is converted first into the alcohol (QI) and then into the corresponding tosyl derivative (RI) according to the methods described in Examples 3 and 4. Finally, the corresponding second generation derivative (SI) is obtained by introducing a pentaerythritol unit on each chain, according to the method described in Example 8.

Reaction scheme

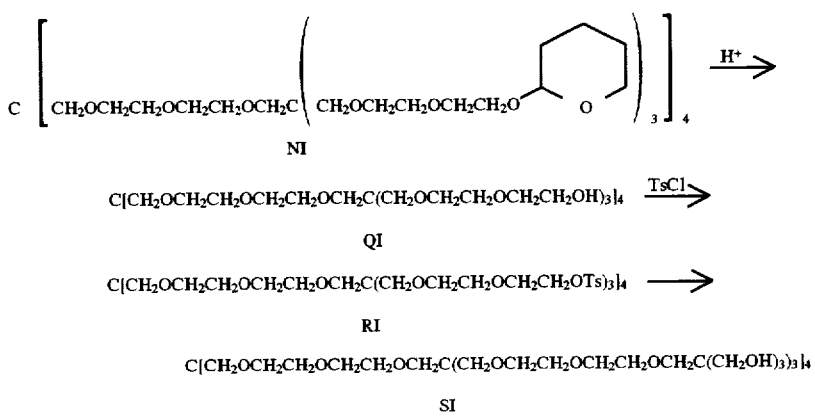

$C[CH_2OCH_2CH_2OCH_2CH_2OCH_2C(CH_2OCH_2CH_2OCH_2CH_2O\text{-pyranyl})_3]_4$

NI $\xrightarrow{TsCl}$ $C[CH_2OCH_2CH_2OCH_2CH_2OCH_2C(CH_2OCH_2CH_2OCH_2CH_2OH)_3]_4$

QI $C[CH_2OCH_2CH_2OCH_2CH_2OCH_2C(CH_2OCH_2CH_2OCH_2CH_2OTs)_3]_4 \longrightarrow$

RI $C[CH_2OCH_2CH_2OCH_2CH_2OCH_2C(CH_2OCH_2CH_2OCH_2CH_2OCH_2C(CH_2OH)_3)_3]_4$

SI

The second generation product

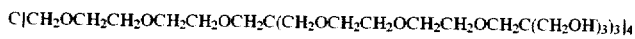

SI was also obtained, after deprotection of the corresponding orthoester, through the following synthetic pathways:

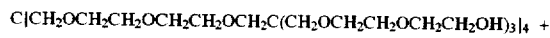

QI

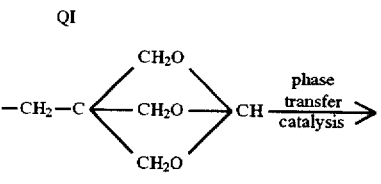

C[CH₂OCH₂CH₂OCH₂CH₂OCH₂C(CH₂OCH₂CH₂OCH₂CH₂OH)₃]₄ +

QI

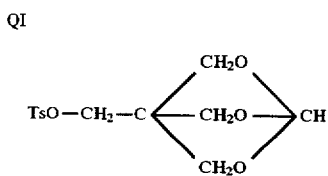

Following similar procedures, products of higher generations were obtained.

EXAMPLE 13
Determination of Limiting Viscosity Numbers (Intrinsic Viscosity) and of Equivalent Viscometric Radii The viscosities of aqueous solutions of compounds of the present invention were determined by measuring the efflux times in an Ubbelohde capillary viscometer controlled by an optical timing detector (AVS, Schott). During the experiments a constant temperature of 37°±0.005° C. was maintained. Density measurements were obtained by a Paar precision densimeter. The numerical evaluation of the limiting viscosity number (or intrinsic viscosity) was obtained from the following relationship $$\frac{\eta - \eta_o}{\eta_o} = \frac{[\eta]c}{1 - k[\eta]c}$$

where c corresponds to the concentration of the macromolecule, $\eta$ is the viscosity of the solution, $\eta_o$ is the viscosity of the pure solvent and k is an empirical parameter. Numerical evaluations of equivalent viscometric radii (r) were obtained by the following relationship $$r = \left(\frac{3[\eta]M}{10\pi N_A}\right)^{1/3}$$

where M is the molar mass of the macromolecule and $N_A$ is Avogadro's number.

Compounds HI, HII and QI have been compared with Tomalia's starburst polyether dendrimers of first and second generation (C[CH₂OCH₂C(CH₂OH)₃]₄ and C[CH₂OCH₂C(CH₂OCH₂C(CH₂OH)₃)₃]₄, respectively, described in Example 11 of U.S. Pat. No. 4,587,329) which do not possess oxyethylene units between the "core" and the first branching point and between the first and the second branching points, and which are characterized by a much more compact structure. Each of these compounds (except Tomalia's compound of second generation) has the same number of surface functional groups, i.e. 12 hydroxyl groups. The results are summarized in Table XXIV.

TABLE XXIV

Limiting viscosity numbers (intrinsic viscosity) and equivalent viscometric radii of new polyoxyethylene branched macromolecules

| Product | Limiting viscosity number $[\eta]$ mL · g⁻¹ (at 37° C.) | Equivalent viscometric radius (r) Å |
|---|---|---|
| TOMALIA, first generation | 2.32 ± 0.06 | 6.08 ± 0.05 |
| HI | 3.38 ± 0.07 | 8.01 ± 0.06 |
| HII | 4.04 ± 0.10 | 9.44 ± 0.08 |
| QI | 4.07 ± 0.04 | 10.92 ± 0.04 |
| TOMALIA, second generation | 2.50 ± 0.03 | 9.30 ± 0.04 |

The data clearly show that the introduction of oxyethylene units gives rise to compounds with radius values which can be even larger than those of higher generation described by Tomalia. With an extremely low, if not absolutely negligeable, "dense-packing" effect there is, as a consequence, the possibility to synthesize molecules up to whatever generation is desired or required for specific uses.

Analogous measurements carried out on macromolecules of successive generations further supported and these statements.

References

1) Tomalia, D. A., Naylor, A. M., and Goddard III, W. A. (1990) Angew. Chem. Int. Ed. Engl. 29, 138–175.
2) Tomalia, D. A., Baker, H., Dewald, J., Hall, M., Kallos, G., Martin, S., Roeck, J., Ryder, J., and Smith, P. (1985) Polymer Journal 17, 117–132.
3) Smith, P. B., Martin, S. J., Hall, M. J., and Tomalia, D. A. In J. Mitchell, Jr., (Ed.): Applied Polymer Analysis and Characterization, Hanser, München/New York 1987, 357–385.
4) Tomalia, D. A., Dewald, J. R. (1986) U.S. Pat. No. 4,587,329.
5) Padias, A. B., Hall Jr., H. K., Tomalia, D. A., and McConnel, J. R. (1987) J. Org. Chem. 52, 5305–5312.
6) Denkewalter, R. G., Kolc, J., Lukasavage, W. J. (1981) U.S. Pat. No. 4,289,872.
7) Newkome, G. R., Yao, Z., Baker, G. R., and Gupta, V. K. (1985) J. Org. Chem. 50, 2003–2004.
8) Newkome, G. R., Yao, Z., Baker, G. R., Gupta, V. K., Russo, P. S. and Saunders, M. J. (1986) J. Amer. Chem. Soc. 108, 849–850.
9) Newkome, G. R., Baker, G. R., Arai, S., Saunders, M. J., Russo, P. S., Therid, K. J. (1990) J. Amer. Chem. Soc. 112, 8458–8465.
10) Newkome, G. R., Moorefield, C. N., Baker, G. R., Johnson, A. L., and Behera, R. K. (1991) Angew. Chem. Int. Ed. Engl. 30, 1176–1178.
11) Newkome, G. R., Moorefield, C. N., Baker, G. R., Saunders, M. J., and Grossman, S. H. (1991) Angew. Chem. Int. Ed. Engl. 30, 1178–1180.

12) Newkome, G. R., Lin, X., and Young, J. K. (1992) Synlett, 53–54.
13) Hawker, C. J., and Frechet, J. M. J. (1990) J. Am. Chem. Soc. 112, 7628–7647.
14) Fréchet, J. M. J., Hawker, C. J., Philippide, A. E. (1991) U.S. Pat. No. 5,041,516.
15) Wooley, K. L., Hawker, C. J., and Fréchet, J. M. J. 1991) J. Am. Chem. Soc. 113, 4252–4261.
16) Wooley, K. L., Hawker, C. J., and Fréchet, J. M. J. (1991) J. Chem. Soc. Perkin. Trans. I, 1059–1076.
17) Fréchet, J. M. J., Hawker, C. J., Uhrich, K. (1992) Patent Appl. WO 9208749.
18) Hawker, C. J., and Fréchet, J. M. J. (1992) J. Chem. Soc. Perkin. Trans. I, 2459–2469.
19) Fréchet, J. M. J., Hawker, C. J., Wooly, K. (1993) Patent Appl. WO 9321259.
20) Buhleier, E., Wehner, W., and Vögtle, F. (1978) Synthesis 155–158.
21) Miller, T. M., Neenan, T. X., Zayas, R., and Bair, H. E. (1992) J. Am. Chem. Soc. 114, 1018–1025.
22) Uchida, H., Kabe, Y., Yoshino, K., Kawamata, A., Tsumuraya, T., and Masamune, S. (1990) J. Am. Chem. Soc. 112, 7077–7079.
23) Mathias, L. J., and Carothers, T. W. (1991) J. Am. Chem. Soc. 113, 4043–4044.
24) Rengan, K., and Engel, R. (1991) J. Chem. Soc. Perkin Trans. I, 987–990.
25) Rengan, K., and Engel, R. (1992) J. Chem. Soc. Chem. Commun., 757–758.
26) Morikawa, A., Kakimoto, M., and Imai, Y. (1991) Macromolecules 24, 3469–3474.
27) Nagasaki, T., Ukon, M., Arimori, S., and Shinkai, S. (1992) J. Chem. Soc. Chem. Commun. 608–610.
28) Serroni, S., Denti, G., Campagna, S., Juris, M., Ciano, M., and Balzani, V., (1992) Angew. Chem. Int. Ed. Engl. 31, 1493–1495.
29) Newkome, G. R., Moorefield, C. N., Behera, R. K. (1993) Patent Appl. WO 9321144.
30) De Brabander-van den Berg, E. M. Mejier, E. W., Vandenbooren, F. H., Bosman, H. J. (1993) Patent Appl. WO 9314147.

We claim:
1. Dendrimeric macromolecules of the formula:

having r number of structures $G_{(1 \to p)}$ in the dendrimer per structure where:

A is a polyfunctional/polyvalent central nucleus, or core, which is an aliphatic open chain, branched or unbranched, or an alicyclic, or a heterocyclic group containing N, O and/or S, or an aromatic or a heteroaromatic group and which contains terminal group to which polyoxaalkylene chains of a first generation shell are attached;

r is an integer from 2 to 10 representing the functionality of the core A and, as a consequence, also the total number of dendra, in which $G_{(1 \to p)}$ is a single dendron linked to A, $|G_{(1 \to p)}|_r$ represents the branched structure of the macromolecule comprising p levels of generation shells from the first one $g_{(1)}$ to the last one $g_{(p)}$, in which the total number of said generation shells p can range from 1 to 20 and in which the different generation shells may contain the same repetition units, and in which:

(a) each generation $g_{(i)}$, except for the last $g_{(p)}$, comprises repeating units, which are represented by a functional group of formula

where:

B is a polyoxaethylene or polyoxapropylene chain of formula:

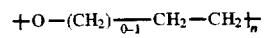

in which n can range from 0 to 25 and may differ from generation to generation and in which in at least one generation shell of the macromolecule, n is other than 0, M represents a branching point which is a polyvalent aliphatic group comprising m reactive functional groups for the linking of the polyoxaalkylene chains of the next generation shell, in which m in an integer ranging from 2 to 5 and m may differ from one generation shell to another;

(b) the last generation shell $g_{(p)}$ comprises functional groups of formula:

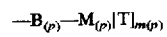

where $B_{(p)}$, $M_{(p)}$, $m_{(p)}$ defined analogously to B, M, and m, with all the $m_{(p)}$ reactive groups of $M_{(p)}$ connected to groups T, in which T is a terminal group that is either H or halo, hydroxyl, amino, thiol, —O-tosyl, —O-mesyl, —O-tresyl, —O-brosyl, trifluoromethanesulfonyl, aldehydo, carboxy or an amido group, said terminal group T being free, either dissociated or undissociated, or protected by a protective group, or $M_{(p)}$ is a single bond, no branching exists and the last generation shell $g_{(p)}$ is formed by groups of formula:

where $B_{(p)}$, and T are as above defined, and (c) when p=1 the macromolecule contains only one generation shell, $g_{(p)}$ which corresponds to $g_{(i)}$ and has the formula:

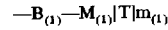

where $B_{(1)}$, $M_{(1)}$, $m_{(1)}$ and T are defined analogously to $B_{(p)}$, $M_{(p)}$, $m_{(p)}$ and T, said macromolecule optionally labeled with an isotope.

2. The macromolecule according to claim 1, wherein a) said "core" A is a neopentyl group of formula:

b) each generation, apart from the last one, comprises growth units of formula:

—B'—M'— wherein

B' is a polyoxyethylene group of formula:

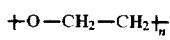

wherein n ranges from 0 to 15 and is the same or different from generation to generation, and is different from 0 in at least one generation.

M' is a branching point with a branching multiplicity of 2 or 3, of formula:

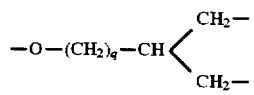

or

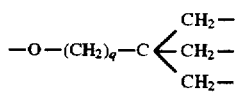

wherein q ranges from 1 to 2;

c) the last generation is a residue of formula:

wherein $B'_p$, $M'_p$ are defined as B', M' and T is defined hereinabove, or $M'_p$ is a single bond, and when $M'_p$ is a single bond, the last generation corresponds to the group:

wherein $B'_p$ and T are as defined above and wherein the total number of generations ranges from 1 to 15.

3. The macromolecule according to claim 2, of formula (III)

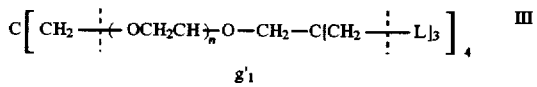

wherein:

n ranges from 0 to 15, and n is different from 0 in at least one generation.

$g'_1$ is the first generation having a branching multiplicity of 3,

L represents T or represents the sequence of successive generations from $g'^2$ to $g'_p$ in which each g', except $g'_p$, is defined as $g'_1$ and the same or a different meaning, whereas $g'_p$ corresponds to $g'^1$-T and the total number of generations g is up to 15.

4. The macromolecule according to claim 1 of formula

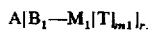

5. The macromolecule according to claim 1 wherein in said formula $A|G_{1 \to p}|_r$ $G_{1 \to p}$ represents $B_1—M_1|G_{2 \to p}|_{m1}$, in which $B_1—M_1$ is $g_1$ and $G_{2 \to p}$ represents $B_2—M_2|G_{3 \to p}|_{m2}$, in which $B_2—M_2$ is $g_2$ until the last generation is reached, in which $G_p$ represents $B_p—M_p|T|_{mp}$.

6. A dendrimeric type macromolecule which is a member selected from the group consisting of a) BI: 1,4,7,11,14,17-hexaoxa-1,17-bis(oxan-2-yl)-9,9-bis|2,5,8-trioxa-8-oxan-2-yl)octyl|heptadecane;

b) BII,III: 1,4,7,10,14,17,20,23-octaoxa-1,23-bis(oxan-2-yl)-12,12-bis|2,5,8,11-tetraoxa-11-(oxan-2-yl)undecyl|tricosane;

c) BIV,V: 1,4,7,10,13,17,20,23,26,29-decaoxa-1,29-bis(oxan-2-yl)-15,15-bis|2,5,8,11,14-pentaoxa-14-(oxan-2-yl)tetradecyl|nonacosane;

d) CI: 3,6,10,13-tetraoxa-8,8-bis-(2,5-dioxa-7-hydroxyheptyl)pentadecan-1,15-diol;

e) CII: 3,6,10,13,16,19-hexaoxa-11,11-bis(2,5,8-trioxa-10-hydroxydecyl)enicosan-1,21-diol;

f) CIII: 14,14-bis(2,5,8,11-tetraoxa-13-hydroxydecyl)-3,6,9,12,16,19,22,25-octaoxaheptacosan-1,27-diol;

g) GI: 3,6,10,13-tetraoxa-8,8-bis(2,5-dioxa-7-bromoheptyl)pentadecan-1,15-dibromide;

h) DI: 1,4,7,11,14,17-hexaoxa-1,17-bis(p-toluensulfonyl)-9,9-bis|2,5,8-trioxa-8-(p-toluenesulfonyl)octyl| heptadecane;

i) DII: 1,4,7,10,14,17,20,23-octaoxa-1,23-bis(p-toluenesulfonyl)-12,12-bis|2,5,8,11-tetraoxa-11-(p-toluenesulfonyl)undecil|tricosane;

j) DIII: 15,15-bis|2,5,8,11,14-pentaoxa-14-(p-toluenesulfonyl)tetradecyl|-1,29-bis(p-toluensulfonyl)-1,4,7,10,13,17,20,23,26,29-decaosanonacosane;

k) EI: 3,6,10,13-tetraoxa-1,15-bis(phthalimido)-8,8-bis|2,5-dioxa-7-(phthalimido)heptyl| pentadecane;

l) EII: 3,6,9,13,16,19-hexaoxa-1,21-bis(phthalimido)-11,11-bis|2,5,8-trioxa-10-(phthalimido) decyl|enicosane;

m) FI: 3,6,10,13-tetraoxa-8,8-bis(2,5-dioxa-7-aminoheptyl)pentadecan-1,15-diamine;

n) HI: 4,7,10,14,17,20-hexaoxa-2,2,22,22-tetra(hydroxymethyl)-12,12-bis|2,5,8-trioxa-10,10-bis(hydroxymethyl)-11-hydroxyundecyl|tricosan-1,23-diol;

o) HII: 18,18-bis|2,5,8,11,14-pentaoxa-16,16-bis(hydroxymethyl)-17-hydroxyheptadecyl|-2,2,34,34-tetra(hydroxymethyl)-4,7,10,13,16,20,23,26,29,32-decaoxapentatriacontan-1,35-diol;

p) LI: 1,23-di(p-toluenesulfonyloxy)-12,12-bis|11-(p-toluenesulfonyloxy)-10,10-bis(p-toluenesulfonyloxymethyl)-2,5,8-trioxaundecyl|-2,2,22,22-tetra(p-toluenesulfonyloxymethyl)-4,7,10,14,17,20-hexaoxatricosane;

q) MI: 1,23-dibromo-12,12-bis|11-bromo-10,10-bis(dibromomethyl)-2,5,8-trioxaundecyl|-2,2,22,22-tetrabromomethyl-4,7,10,14,17,20-exaoxatricosane;

r) NI: 1,35-di(oxan-2-yl-oxy)-18,18-bis|17-(oxan-2-yl-oxy)-10,10-bis(7-(oxan-2-yl-oxy)-2,5-dioxaheptyl)-2,5,8,12,15-pentaoxaheptadecyl|-8,8,28,28-tetra|(7-oxan-2-yl-oxy)-2,5-dioxaheptyl|-3,6,10,13,16,20,23,26,30,33-decaoxapentatricontane.

7. The macromolecule of claim 1 labeled with $^{13}C$, $^{14}C$, $^2H$, $^3H$ or, $^{125}I$.

8. A dendrimeric macromolecule consisting of a core, and at least two cascade branched chains linked to said core, wherein said core is a polyvalent organic molecule and said branched chains comprise a plurality of repeating units, said units being the same or different from one generation shell to another, each of said units consisting of (a) a polyoxaalkylene chain, and
(b) a polyvalent branched aliphatic group having further branching points attached to it;

said dendrimeric macromolecule having at the most 20 generation shells of said repeating units, the last of said generation shells having mono- or polyvalent functional terminal groups; and said polyoxaalkylene chain consists of n oxyalkylene group wherein n is an integer ranging from 0 to 25 and is the same or different from one generation shell to another and at least in one of said generation shells is other than 0.

* * * * *